(12) United States Patent
Asmar

(10) Patent No.: US 6,511,436 B1
(45) Date of Patent: Jan. 28, 2003

(54) DEVICE FOR ASSESSING CARDIOVASCULAR FUNCTION, PHYSIOLOGICAL CONDITION, AND METHOD THEREOF

(76) Inventor: Roland Asmar, 11 Bis Boulevard Delessert, Paris (FR), 75016

( * ) Notice: Subject to any disclaimer, the term of this patent is extended or adjusted under 35 U.S.C. 154(b) by 0 days.

(21) Appl. No.: 09/596,273

(22) Filed: Jun. 16, 2000

(30) Foreign Application Priority Data

Jun. 16, 1999 (FR) .......................................... 99/07632

(51) Int. Cl.$^7$ ................................................. A61B 5/02

(52) U.S. Cl. ........................ 600/500; 600/504; 600/481

(58) Field of Search ................................ 600/490, 405, 600/481, 500–504

(56) References Cited

U.S. PATENT DOCUMENTS

| | | | | |
|---|---|---|---|---|
| 3,090,377 A | | 5/1963 | Salisbury et al. ........... | 128/2.05 |
| 4,425,922 A | | 1/1984 | Conti et al. ................. | 128/691 |
| 5,316,004 A | | 5/1994 | Chesney et al. ............ | 128/672 |
| 5,564,427 A | * | 10/1996 | Aso et al. ................... | 128/681 |
| 5,724,981 A | | 3/1998 | Apple ......................... | 128/687 |
| 5,876,347 A | | 3/1999 | Chesney et al. ............ | 600/485 |
| 6,120,459 A | * | 9/2000 | Nitzan et al. ............... | 600/493 |
| 6,152,879 A | * | 11/2000 | Mohler ....................... | 600/485 |

FOREIGN PATENT DOCUMENTS

| | | | | |
|---|---|---|---|---|
| DE | 405 186 | | 2/1941 | .................. 30/402 |
| DE | 704 186 | | 2/1941 | .................. 30/402 |
| DE | 845 379 | | 7/1952 | .................. 30/402 |
| DE | 198 18 147 | | 11/1999 | |
| EP | 2 481 917 | | 11/1981 | ............ A61B/5/02 |
| EP | 0 443 267 A1 | * | 8/1991 | ......... A61B/5/0285 |

OTHER PUBLICATIONS

Benthin et al., "Calculation of Pulse–Wave Velocity Using Cross Correlation—Effects of Reflexes in the Arterial Tree," *Ultrasound in Med. & Bio.* vol. 17, No. 5, pp. 461–469 (1991).

Weinman et al., "Equipment for Continuous Measurements of Pulse Wave Velocities," *Med. & Bio. Engineering* vol. 9, pp. 125–136 (1971).

Ramsey et al., "Real–time Measurements of Pulse Wave Velocity from Arterial Pressure Waveforms," *Medical & Biol. Engin. & Computing* pp. 636–642 (1995).

Asmar, "Pulse Wave Velocity Principles And Measurement," *Arterial Stiffness and Pulse Wave Velocity*, 1999; ; Ch. III: 25–55, mé scientifiques et médicales Elsevier SAS.

Asmar et al., "Assessment Of Arterial Distensibility By Automatic Pulse Wave Velocity Measurement—Validation And Clinical Application Studies," *Hypertension* 1995; vol. 26 No. 3: 485–490.

Asmar et al., "Non–Invasive Evaluation Of Arterial Abnormalities In Hypertensive Patients," *Journal of Hypertension* 1997; vol. 15 (suppl 2): S99–S107.

Benetos et al., "Large Artery Stiffness In Hypertension," *Journal of Hypertension,* 1997; vol. 15 (suppl. 2): S89–S97.

Blacher et al., "Aortic Pulse Wave Velocity As A Marker Of Cardiovascular Risk In Hypertensive Patients," *Hypertension,* 1999; 33: 1111–1117.

(List continued on next page.)

*Primary Examiner*—Kevin Shaver
*Assistant Examiner*—Patricia C. Mallari
(74) *Attorney, Agent, or Firm*—Testa, Hurwitz & Thibeault, LLP

(57) ABSTRACT

A device to evaluate the arterial wall stiffness using pulse wave velocity measurements is described. The device uses probes to record the pulse wave at different locations on the body. Automatic calculation of the time delay between the proximal and distal waves is performed. Based on the pulse wave velocity values and the brachial pulse pressure, an estimation of the central (aortic) pulse pressure is calculated.

37 Claims, 11 Drawing Sheets

OTHER PUBLICATIONS

Blacher et al., "Impact Of Aortic Stiffness On Survival In End–," *Circulation*, 1999; 99: 2434–2439.

Arnold et al., "Large Artery Function In Patients With Chronic Heart Failure," *Circulation*, 1991; 84: 2418–2425.

Asmar et al., "Aortic Distensibility in Normontensive, Untreated and Treated Hypertensive Patients," *Blood Pressure* 1995; 4: 48–54.

Asmar et al., "Arterial Distensibility and Ambulatory Blood Pressure Monitoring in Essential Hypertension," *Am J Cardiol* 1988; 61: 1066–1070.

Asmar et al., "Cardiac Hypertrophy and Arterial Compliance Following Drug Treatment in Hypertension," *Journal of Cardiovascular Pharmacology* 1991; 18 (Suppl. 7): S37–S39.

Asmar et al., "Arterial and Cardiac Changes in Hypertension in the Elderly," *Blood Pressure* 1995; 4 (Suppl. 3): 31–37.

Avolio, "Pulse Wave Velocity and Hypertension," *Arterial and Venous Systems In Eneutral Hypertension* Safar ME. (Ed) pp. 133–152.

Barenbrock et al., "Different Effects of Hypertension, Atherosclerosis and Hyperlipidaemia on Arterial Distensibility," *Journal of Hypertension* 1995; 13: 1712–1717.

Bazett et al., "Measurements of Pulse Wave Velocity," *American Journal of Physiology*, 192263, 94–116 (1922).

Benetos et al., "Heterogeneity of the Arterial Tree in Essential Hypertension: A Noninvasive Study of the Terminal Aorta and the Common Cartoid Artery," *Journal of Human Hypertension* (1994) 8, 501–507.

Beyerholm, "Studies of the Velocity of Transmission of the Pulse Wave in Different Pathological Conditions (Principally Arteriosclerosis With and Without Hypertonia, and Heart–Arythmiae)," *Aeta Med. Scandinav.* 1922; 67:323–352.

Beyerholm, "Studies of the Velocity of Transmission of the Pulse Wave in Normal Individuals," *Aeta med. Scandinav.* 1922; 67: 203–235.

Blacher et al., "Cartoid Arterial Stiffness as a Predictor of Cardiovascular and All–Cause Mortality in End–Stage Renal Disease," *Hypertension*, 1998; 32: 570–574.

Bramwell et al., "Velocity of Transmission of the Pulse –Wave and Elesticity of Arteries," *The Lancet*, 1922; p. 891.

Christensen et al., "Arterial Wall Stiffness In Insulin–Dependent Diabetes Mellitus An In Vivo Study," *Acta Radiologica* 28 (1987) Fasc. 2 pp. 207–208.

Dart et al., "Aoritc Distensibility in Patients With Isolated Hyperchloesterolaemia, Coronary Artery Disease, or Cardiac Transplant," *Lancet*, 1991; 338: 270–73.

Eliakim et al., "Pulse Wave Velocity In Healthy Subjects and in Patients With Various Disease States," *American Heart Journal*, 1971; 82:4, pp. 448–457.

Gribbin et al., "Arterial Distensibility In Normal and Hypertensive Man," *Clinical Science* 1979; 56: pp. 413–417.

Hallock, "Arterial Elasticity In Man Relation To Age As Evaluated By The Pulse Wave Velocity Method," *Arch Int. Med.*, 1936; 54: 770–798.

Haynes et al., "Pulse Wave Velocity and Arterial Elasticity in Arterial Hypertension, Arteriosclerosis, and Related Conditions," *Am Heart Journal*, 1936; vol. 11, No. 4: 385–401.

Hickson et al., "The Effect of Variations in Blood–Pressure on Pulse Wave Velocity in the Brachial Artery in Man," *Journal of Physiology*, 1922; 59: 217–220.

Hirai et al., "Stiffness of Systemic Arteries in Patients With Myocardial Infarction—A Noninvasive Method to Predict Severity of Coronary Atherosclerosis," *Circulation* 1989; 80: 78–86.

Kelly et al., "Noninvasive Determination of Age–Related Changes in the Human Arterial Pulse," *Circulation* 1989; 80: 165201659.

Laurent, "Arterial Wall Hypertrophy and Stiffness in Essential Hypertensive Patients," *Hypertension* 1995; 26: 355–362.

Lax et al., "Abnormalities of the Arterial Pulse Wave in Young Diabetic Subjects," *Circulation* 1959; vol. XX: 1106–1110.

Lehmann, "Aortic Distensibility and Hypercholesterolaemia," *Lancet* 1992; 340: 1171–1172.

Lehmann et al., "A Blood Pressure Independent Index of Aortic Distensibility," *The British Journal of Radiology* 1993; 66: 126–131.

Lo et al., "Doppler Ultrasound Recognition of Preclinical Changes in Arterial Wall in Diabetic Subjects: Compliance and Pulse–Wave Damping," *Diabetes Care* 1986; 9: 27–31.

Okada et al., "Role of Pulse Wave Velocity For Assessing Autonomic Nervous System Activities in Reference to Heart Rate Variability," *Med. Inform.* 1996; 21: No. 1, 81–90.

Safar et al., "Increased Pulse Pressure in Patients with Arteriosclerosis Obliterans of the Lower Limbs," *Arteriosclerosis* 1987; 7: 232–237.

Safar et al., "Recent Advances on Large Arteries in Hypertension," *Hypertension* 1998; 32: 156–161.

Sands, "Studies In Pulse Wave Velocity," *Am. J. Physiol.* 1925; 71: 519–533.

Scarpello et al, "Ultrasound Measurements of Pulse–Wave Velocity in the Peripheral Arteries of Diabetic Subjects," *Clinical Science* 19880; 58: 53–57.

Smilde et al., "Carotid and Femoral Artery Wall Thickness and Stiffness in Patients at Risk for Cardiovascular Disease," *Arterioscler Thromb Vasc Biol.* 1998; 18: 1958–1963.

Smulyan et al., "Forearm Arterial Distensibility in Systolic Hypertension," *JACC* 1984; vol. 3, No. 2: 387–393.

Steele, "Interpretation of Arterial Elasticity From Measurements of Pulse Wave Velocities," *Am. Heart Journal* 1937; 7: 452–465.

Tanokuchi et al., "Factors Related to Aortic Pulse–Wave Velocity in Patients with Non–Insulin–Dependent Diabetes Mellitus," *Journal of International Medical Research* 1995; 23: 423–430.

Toto–Moukouo et al., "Pulse Wave Velocity in Patients with Obesity and Hypertension," *Am. Heart J.* 1986; 112: 136–140.

Wilkinson et al., "Reproducibility of Pulse Wave Velocity and Augmentation Index Measured by Pulse Wave Anaylsis," *J. Hypertens* 1998; 16: 2079–2084.

Woolam et al., "The Pulse Wave Velocity as an early Indicator of Atheroclerosis in Diabetic Subjects," *Ucirculation 1962; vol. XXV:* 532–539.

Topouchian et al., "Changes in Arterial Structure and Function Under Trandolapril–Verapamil Combination in Hypertension" Stroke 1999; 30: 1056–1064.

Maldonado et al., "Estrogen Replacement Therapy Don't Change Blood Pressure But Decrease Pulse Wave Velocity In Normotensive Posmenopausal Women" AJH 1998; 11: 95A.

Asmar et al., "Reversion of Arterial Abnormalities By Long–Term Antihypertensive Therapy In Large Population—The Complior®Study" Journal of Hypertension 1999; vol. 17 (suppl 3): S9–S10.

Asmar et al., "Arterial Distensibility and Circadian Blood Pressure Variability" Blood Pressure Monitoring 1996; 1: 333–338.

Ribeiro et al., "Arterial Distensibility in Subjects with White–Coat Hypertension With and Without Diabetes or Dyslipidaemia: Comparison With Normotensives and Sustained Hypertensives" Blood Press Monit 2000; 5: 11–17.

Bortolotto et al., "Plasma Homocysteine, Aortic Stiffness, and Renal Function in Hypertensive Patients" Hypertension 1999; 34 [part 2]: 837–842.

Boutouyrie, et al., "Common carotid artery stiffness and patterns of left ventricular hypertrophy in hypertensive patients," *Hypertension* 25:651–659 (1995).

Bramwell et al., "The velocity of the pulse wave in man," *Proceeding of Royal Society* (London) 96:298–306 (1922).

Draaijer et al., "Vascular distensibility and compliance in salt–sensitive and salt–resistant borderline hypertension," *Journal of Hypertension* 11:119–1207 (1993).

Girerd et al., "Arterial distensibility and left ventricular hypertrophy in patients with sustained essential hypertension," *American Heart Journal* 122:1210–1214 (1991).

Gibbin et al., "Arterial distensibility in normal and hypertensive man," *Clinical Science* 56:413–417 (1979).

Hallock, "Arterial elasticity in man in relation to age evaluated by the pulse wave velocity method," *Archives of Internal Medicine* 54:770 (1934).

Hickson et al., "The effect of variations in blood–pressure on pulse wave velocity in the brachial artery in man," *Journal of Physiology* 59:227–220 (1924).

Kelly et al., "Arterial dilation and reduced wave reflection," *Hypertension* 14:14–21 (1989).

Latham, "Pulse propagation in the systemic arterial tree," In: Westerhof, N., Gross, D.R. (eds.), Vascular Dynamic: Physiological perspectives. New York and London: Plenum Press, pp. 49–68 (1989).

Lehmann et al., "Validation and reproducibility of pressure–corrected aortic distensibility measurements using pulse–wave–velocity Doppler ultrasound," *J. Biomed. Eng.* 15:221–228 (1993).

Lehmann et al., "Aortic compliance measurements using Doppler ultrasound: in vivo biochemical correlates," *Ultrasound in Medicine and Biology* 19:683–710 (1993).

London, "Large artery function and alterations in hypertension," *Journal of Hypertension* 13 (Supp 2):S35–S38) (1995).

McDonald, "Blood flow in arteries: theorical, experimental and clinical principles," $4^{th}$ ed. London, Arnold, pp. 77–142 (1996).

McDonald, "Blood flow in arteries: theorical, experimental and clinical principles," $4^{th}$ ed. London, Arnold, pp. 16–269 (1996).

McDonald, "Blood flow in arteries: theorical, experimental and clinical principles," $4^{th}$ ed. London, Arnold, pp. 283–359 (1996).

McDonald, "Blood flow in arteries: theorical, experimental and clinical principles," $4^{th}$ ed. London, Arnold, pp. 398–437 (1996).

Moritani et al., "Arterial pulse wave velocity, Fourier pulsatility index, and blood lipid profiles," *Medicine and Science in Sports and Exercise* 19:404–409 (1987).

Newman, "Changes in aortic distensibility and area ratio with the development of atherosclerosis," *Atherosclerosis* 14:231–240 (1971).

Safar et al., "The arterial system in hypertension. A prospective view," *Hypertension* 26:10–14 (1995).

Simonson et al., "Contour of the toe pulse, reactive hyperemia, and pulse transmission velocity: group and repeat variability, effect of age, exercise, and disease," *American Heart Journal* 50:260–2796 (1995).

Stella et al., "Elastic modulus in young diabetic patients (ultrasound measurements of pulse wave velocity)," *Angiology* 35:729–734 (1984).

Taylor, "Wave travel in arteries and the design of the cardiovascular system," In: Attinger EO (ed.), Pulsatile Blood Flow. New York: McGraw Hill, pp. 343–347 (1964).

Turner et al., "Pulse wave velocity under varying conditions in normal and abnormal human cardiovascular systems," *Journal of Clinical Investigations* 4:430 (1927).

Benetos et al., "Large artery stiffness in hypertension," *Journal of Hypertension* 15 (Supp 2):S89–S97 (1997).

Asmar et al., "Assessment of Arterial Distensibility by Automatic Pulse Wave Velocity Measurement," *Hypertension* 26(3):486–490 (1995).

Colson Maitriser la technologie, Compilor II, Manual for Use.

* cited by examiner

RECORDINGS OF PULSE WAVES AND RESPIRATION-CAROTID ARTERY, REPIRATION, RADIAL ARTERY.

RELATIONSHIP BETWEEN BODY MASS INDEX AND BRACHIAL-RADIAL PWV IN OBESE AND NON-OBESE HYPERTENSIVE PATIENTS.

DEVICE FOR ASSESSING CARDIOVASCULAR FUNCTION, PHYSIOLOGICAL CONDITION, AND METHOD THEREOF

CROSS-REFERENCE TO RELATED APPLICATIONS

This application claims priority under 35 U.S.C. §119 to and is based on French Patent Application No. 9907632, filed Jun. 16, 1999, the entirety incorporated by reference herein.

TECHNICAL FIELD OF THE INVENTION

This invention relates to the field of cardiovascular medicine and whole body medicine and consists of a new system and device for assessing cardiovascular function in which arterial distensibility and stiffness is determined from pulse wave velocity, and method thereof.

BACKGROUND OF THE INVENTION

Cardiovascular disease is a leading cause of morbidity and mortality in most industrialized nations. Large-artery pathology is the major contributor to cardiovascular disease. Changes to the arterial wall are usually associated with age, smoking, diabetes, dyslipidemia, hypertension, and other known factors. Thus, arteries constitute the target site and the common denominator of cardiovascular risk factor complications.

Most noninvasive methods for assessing the condition of large arteries are costly and generally are within the purview of only a limited number of clinical research laboratories. In a more typical clinical setting, simpler methods are required for large-artery assessment. Arterial pulse wave velocity is a simple, noninvasive, accurate, and reproducible method for assessing arterial stiffness and distensibility. Pulse wave velocity is related to the geometry, the structure, and the function of the arterial wall. The arterial pulse is a fluctuation caused by heart contraction and occurs at the same frequency as the heart rate. The ejection of blood from the left ventricle through the aortic valve in the aorta leads to flow, pressure, and diameter pulsations throughout the arterial tree.

The basic principle behind arterial pulse wave velocity measurement is that the pulse wave generated by left ventricular ejection is propagated along the arterial tree at a speed determined by the elastic and geometric properties of the arterial wall, and by blood density. The material properties of the arterial wall, its thickness, the lumen diameter, and factors such as age and blood pressure levels, among others, are considered to be the major determinants of pulse wave velocity. Measurement of the pulse wave velocity is based on the determination of the time delay between two pulse waves recorded at two distinct sites along the arterial system, using a separate specific transducer at each site. The distance traveled by the pulse wave is obtained from measurements of the distance between the two recording sites. Pulse wave velocity is calculated from measurements of the pulse transit time and the distance traveled by the pulse between the two recording sites.

The determination of the time delay between the pressure waves, recorded at two distinct points of the arterial system, is currently performed using continuous recordings of the pressure curves traces generated by the pulse wave. These recorded curves represent the typical pressure wave peaks corresponding to a single heart-beat. To determine the transit time using this method, the time delay between the two maximal peaks of the pressure wave corresponding to the same pulse is calculated. This interval can be obtained by direct measurement from the printed curve traces of the two recordings. However, maximal peak determinations are variable, depending on several clinical and biological parameters such as gender, height, weight, heart rate, pulse wave reflection, and age. Thus, the precision of the time interval determination may be poor and may limit the overall quality of the measurement using previously known methods and devices to measure pulse wave velocity.

SUMMARY OF THE INVENTION

The present invention provides a system, device, and noninvasive method for the automatic determination of the pulse wave transit time between two recording sites ($M_1$, $M_2$) in a mammalian arterial system, according to a procedure that involves the following stages:

a) Application of a pressure-sensitive transducer at each recording site of the arterial system.

b) Recording of the pulse wave at each of the two recording points.

c) Calculation of the pulse wave time interval between the two recording sites as follows:

$c_1$) At the first recording site, the determination on the proximal waveform of the time $t_1$ by identifying the foot of the wave at the beginning of the initial upstroke.

$c_2$) At the second recording site, the determination on the distal waveform of the time $t_2$ corresponding to the same pulse wave by identifying of the foot of the wave.

$c_3$) Determination of the transit time from the time delay between the two corresponding waveforms, the proximal ($t_1$) and the distal ($t_2$) pulse waveforms.

In addition, the current invention allows the calculation of the pulse wave velocity between the two recording sites and the evaluation of the aortic pulse pressure from the previously determined pulse wave velocity.

BRIEF DESCRIPTION OF THE DRAWING

In the drawings, like reference characters generally refer to the same parts throughout the different views. The drawings are not necessarily to scale, emphasis instead generally being placed upon illustrating the principles of the invention.

DETAILED DESCRIPTION OF THE INVENTION

In general, in one aspect, the invention is a device and system for non-invasive and automatic assessment of cardiovascular function in a mammal. In another aspect, the invention is a method for assessing cardiovascular function in a mammal. The device, system, and method of the invention are used to assess cardiovascular function or systemic physiological condition in a patient to provide baseline information concerning a patient's cardiovascular or systemic physiological status for the diagnosis and prognosis of cardiovascular disease, or other diseases, or as a means for monitoring a patient's response to therapy. In particular clinical applications, the device, system, and method according to the invention, are used to assess cardiovascular function in, for example, hypertension, diabetes, dyslipidemia, arteriosclerosis and atherosclerosis, coronary heart disease, cerebrovascular disease, congestive heart failure, peripheral vascular disease, Marfan's syndrome, Ehlers-Danlos syndrome, aortic aneurysm, renal disease, cardiac arrhythmias, hypopituitarism, smoking, thyroid dysfunction, sleep apnea, and hypotension, to name a few.

Referring to FIGS. 1A–1D, in one embodiment, the system according to the invention, includes at least two transducers or probes 14, 16, a central processing unit 10 such as a personal computer, a display 11, a data acquisition system 12, an analog to digital converter, and an apparatus for measuring distance. In general, arterial hemodynamic behavior in the form of an arterial pulse wave, is acquired from a patient with transducers placed on the patient's skin at at least two arterial recording sites where the arteries pass very close to the skin surface or where the pulse is otherwise available for recording. The arterial pulse signal is obtained in analog form at the least two recording sites, converted to a digital signal by an analog to digital converter, and projected onto a central processing unit through a data acquisition system. The data acquisition system collects a predetermined sample of the arterial pulse waveform after digitization by the analog to digital converter. The central processing unit analyzes the pulse wave form and extracts the pulse wave velocity from the arterial hemodynamic behavior and the measured distance between arterial recording sites, to provide an assessment of the patient's cardiovascular function or systemic physiological status. The assessed cardiovascular or physiological status of a patient may be displayed on a suitable display numerically, graphically, or by some other means. A suitable display includes an LCD or any other display such as a scope, LED, or CRT. The assessed patient cardiovascular function may be compared to a pre-programmed library of normal and pathologic patient cardiovascular function, a reference value, a known standard value, or to the patient's own cardiovascular function assessed at one or more earlier points in time.

Figure 2:
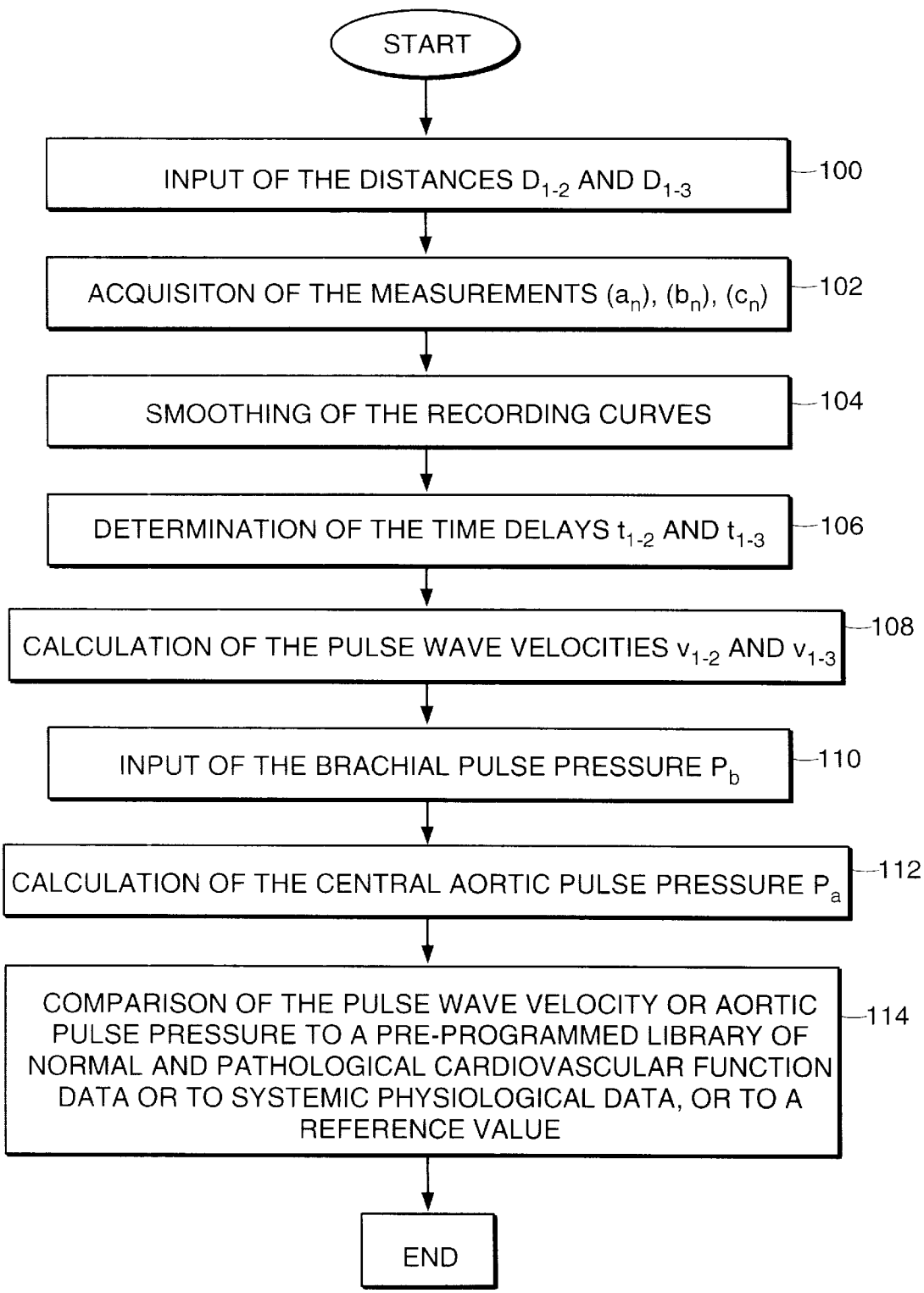
FIG. 2 is a schematic flowchart displaying the different stages of the method of the invention.

FIG. 2 depicts a signal processing schematic of one embodiment of the invention. At step 102, arterial pulse wave data is acquired by at least two transducers. The arterial pulse wave is related to three different pulsations: flow, pressure (pressure/volume), and arterial diameter fluctuations. The transducers, according to the invention, measure pulse pressure, pulse volume, pulse flow, or arterial diameter by non-invasive means such as ultrasound and plethysmography.

The pressure/volume pulse, for example, can be measured non-invasively by pressure/volume-sensitive transducers. Their application may be applied only to superficial arteries where the pulse is palpable. External pulse recordings of this type usually employ air or fluid-containing capsules placed over the pulse points. The volume/pressure pulsations of an artery are transmitted radially and then are detected by the capsules and magnified by displacement of the air or fluid in the capsule. Alternative methods for measuring volume/pressure pulsations include Doppler or piezoelectric quartz means.

Alternatively, pressure/volume pulse recording may be employed using plethysmography. This method measures the volume variations using a mercury-filled silastic tube (mercury plethysmography) or a light source and a photo detector (photoplethysmography) or by other means. In yet another embodiment, tonometer principles can be applied to peripheral arterial pressure measurements.

The pulsatile blood flow, generated by left ventricular myocardial contraction and blood ejection into the aorta and arterial tree, can be measured by non-invasive Doppler transducers. This method can detect the flow pulse in the superficial peripheral arteries as well as less externally palpable arteries, such as the aorta.

Measurements of fluctuations in arterial diameter may also be used to detect the arterial pulse wave. In this method, the amplitude of the diameter fluctuation is small compared to the fluctuations in pressure and pulse waves and its measurement should be performed using a sophisticated method based on ultrasound technique.

The method, according to the invention, for measuring pulse wave velocity, includes recordation of a proximal pulse wave and a distal pulse wave at proximal and distal recording sites on the arterial tree. The pulse wave recorded at the two recording sites may be recorded sequentially. In a particular embodiment, the proximal and distal pulse waves are recorded simultaneously from separate transducers at the proximal and distal recording sites on the arterial tree to record the real traveling velocity of the same wave.

Figure 1A:
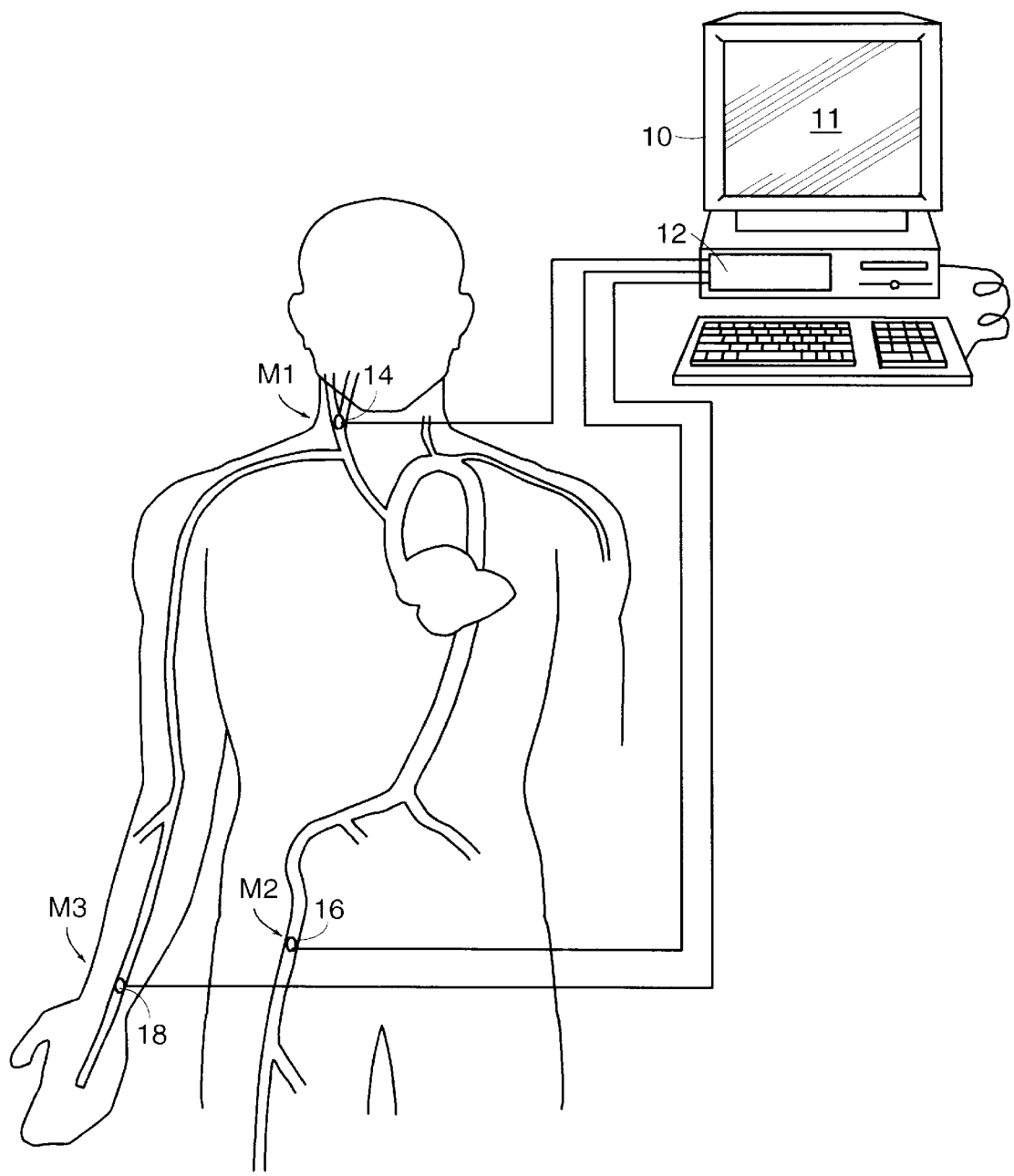
FIG. 1A is a schematic representation of the system of the invention.
Figure 1B:
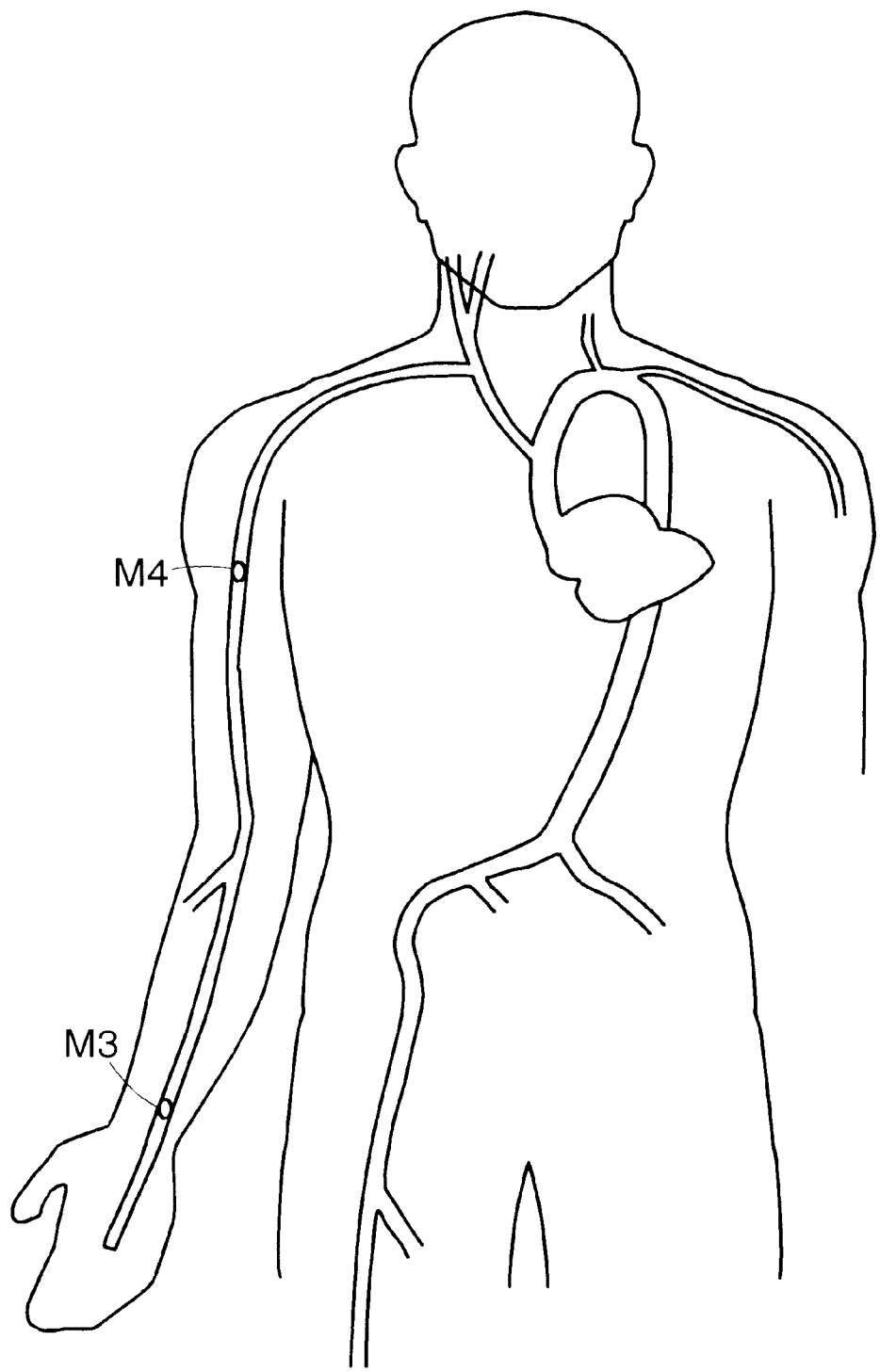
FIG. 1B is a schematic of arterial recording sites on a patient's body.
Figure 1C:
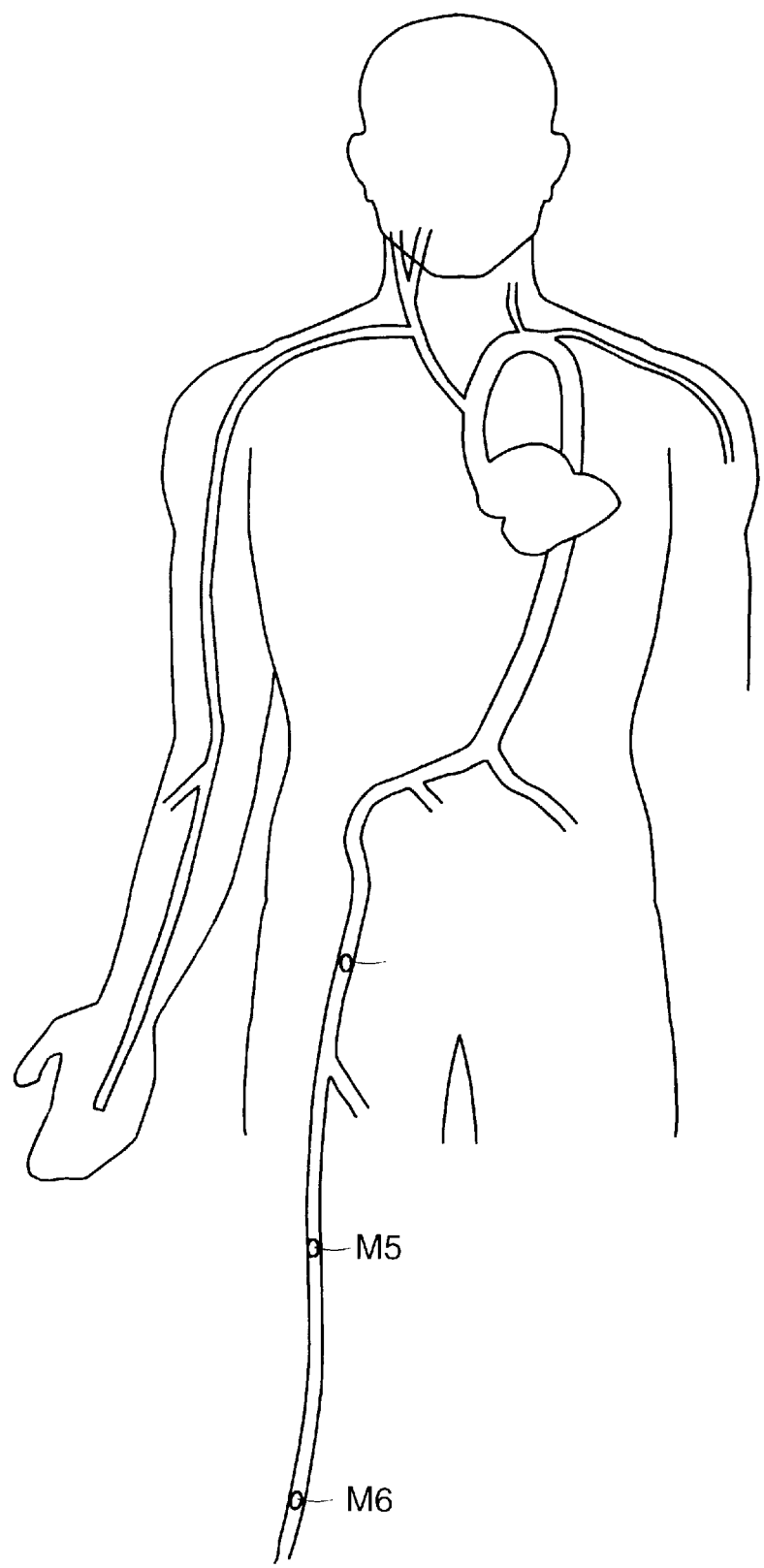
FIG. 1C is another schematic of arterial recording sites on a patient's body
Figure 1D:
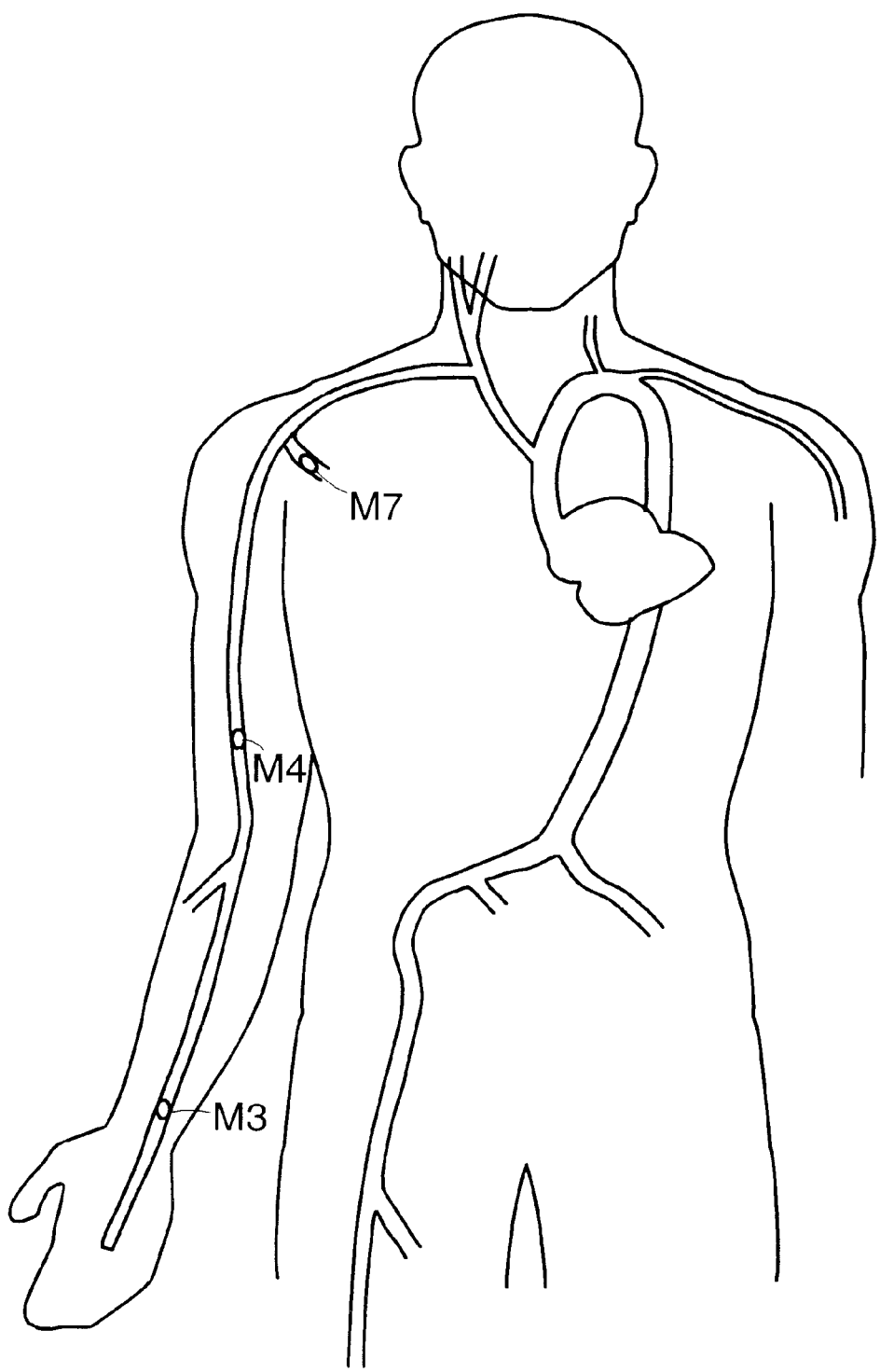
FIG. 1D is yet another schematic of arterial recording sites on a patient's body

In one embodiment of the invention, illustrated in FIG. 1A, a first transducer 14 is placed on the skin of a patient's neck overlying the common carotid artery at a first (proximal) arterial site $M_1$. A second transducer 16 is placed on the skin of the patient's leg overlying the patient's femoral artery at $M_2$, a second (distal) arterial site. In this configuration, the pulse wave velocity can be measured between the carotid artery and the femoral artery to assess aorta-iliac arterial stiffness. In another embodiment, still referring to FIG. 1A, in this scheme, a third transducer 18 may be placed on the skin of the distal extremity of the patient's forearm overlying the radial artery at $M_3$. Additional transducers may be used to record pulse wave at still other superficial arterial recording sites.

The system for assessing cardiovascular function is not limited to just the embodiment illustrated. The transducer positions may be altered by the operator for the study of other arterial segments. For the study of arterial hemodynamic behavior at the brachial-radial segment, for example, illustrated in FIG. 1B, the first transducer 14 is placed on the skin overlying the brachial artery at $M_4$, and the second transducer 18 is placed over the skin of the arm overlying the radial artery at $M_3$. The transducers can be placed on any superficial arterial sites or other suitable site for recordation of pulse, such as the tibial $M_5$, or pedious arteries $M_6$ shown in FIG. 1C, to evaluate the stiffness of the arteries of the lower limb, or between the subclavian (axillary) artery $M_7$ and the radial $M_3$ or brachial $M_4$ artery illustrated in FIG. 1D to evaluate arterial stiffness of the upper limb. Other combinations of arterial recording sites are also contemplated by the invention and are not limited to only those illustrated. The transducer may be applied or attached to the patient's skin overlying the appropriate arterial site using a rubber band, suction cups, adhesive tape, adhesive, Velcro®, hook and loop fasteners, or any other means of attachment known to one skilled in the art.

Referring again to FIG. 1A, the central data processing unit 10 is a dedicated digital signal processor, personal computer, or other type of processing unit. The central data processing unit 10 also includes a data acquisition system 12 that provides the connection of the transducers to the central data processing unit 10.

Referring now to FIG. 2, in the first step 100, the operator inputs into the central processing unit the distance between the transducers measured by a measuring apparatus. The measurement may be taken by a tape measure or other device such as a rolling device similar to a map distance measuring device. Alternatively, the distance measurement may be calculated from inputted patient data such as height, age, weight, body confirmation, or other patient values. The distance between the two transducers used for pulse recordings may be determined at the beginning or at the end of the examination; the order of this step in relation to other steps is not critical. The distance data is ultimately required before calculation of the pulse wave velocity can be determined.

For example, in the system illustrated in FIG. 1A, the distance $d_{1-2}$ between transducer 14 at $M_1$, and transducer 16 at $M_2$ or the distance $d_{1-3}$ between transducer 14 at $M_1$ and transducer 18 at $M_3$ is inputted.

Referring again to FIG. 2, in the next step 102, simultaneous recordings of the arterial pulse at a plurality of arterial recording sites, for example, $M_1$, $M_2$, and $M_3$ from the transducers 14, 16, and 18 and the acquisition card 12 are obtained at a predetermined time interval by the central data-processing unit 10. In a particular embodiment of the invention, the duration of the data acquired is 15 seconds. Other data acquisitions times are also contemplated by the invention. For example, data may be acquired over a 12, 24–48 hour or other time periods. In yet another particular embodiment of the invention, recordings are made over at least ten or more successive heartbeats in order to cover the variability in arterial pulse that occurs during at least one complete respiratory cycle.

At step 102, the central data-processing unit 10 records on a hardware storage device such as random access memory or a hard disk, three series of discrete arterial pulse measurements ($a_n$, $b_n$, $c_n$) taken at acquisition times separated by a constant interval determined by the acquisition card 12. Following the recording of the $a_n$, $b_n$, and $c_n$ measurements, each recording is smoothed (step 104) so as to filter out the high frequency noise that is typically present in the actual measurements. To this end, a low-pass filtering algorithm, such as the following one, is used to process each recording. Other low-pass filtering algorithms also may be used. For brevity, the low-pass filtering algorithm is shown only for the $a_n$ recording, as follows:

```
for i:=2 to N-1 do
    mean :=(a[i-1]+a[i]+a[i+1])/3;
    d1 :=abs(a[i-1]-mean);
    d2 :=abs(a[i]-mean);
    d3 :=abs(a[i+1]-mean);
    if d1<d2 then a[i]: a[i-1]; fi;
    if d3<d2 then a[i]:=a[i+1]; fi;
```

Figure 3:
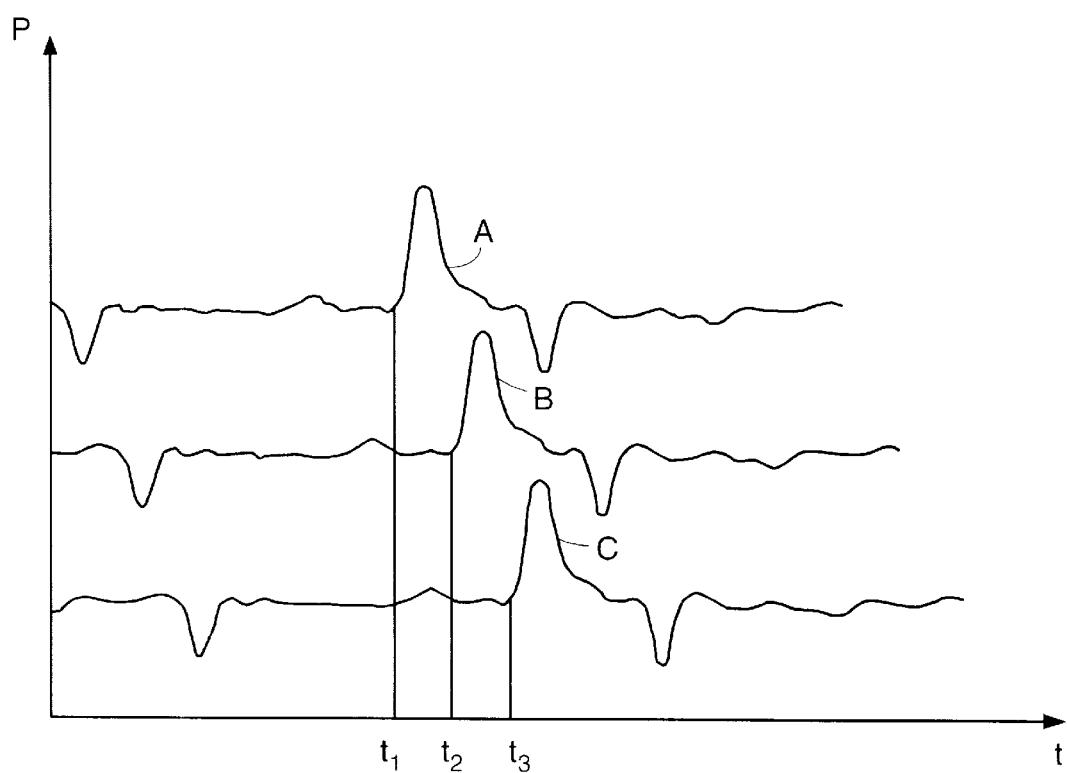
FIG. 3 is an illustrative example of the blood pressure wave measurements recorded at three sites of the human arterial system.

After filtering the recording as detailed above, curves A, B, C, such as those shown in FIG. 3, are obtained from the recording sites where $a_n$ is the recording at the first recording site $M_1$, $b_n$ is the recording at the second recording site $M_2$, and $c_n$ is the recording at the third recording site $M_3$, respectively. The curves A, B, C represent the time evolution of the pulse arterial waveform recorded at arterial recording sites $M_1$, $M_2$, and $M_3$. It should be noted that each of these waveforms reaches the corresponding recording site with some time delay.

In the next step 106, the central data-processing unit 10 determines, from the analysis of the two pairs of recordings $a_n$ and $b_n$ and $a_n$ and $c_n$, the time delays between the time course of the same pressure wave at $M_1$ and $M_2$, and at $M_1$ and $M_3$. These time intervals correspond to $t_{1-2}$ and $t_{1-3}$, respectively.

The same algorithm is used for the calculation of the $t_{1-2}$ and $t_{1-3}$ intervals. In the interest of brevity only the calculation of the time delay $t_{1-2}$ is presented and described below. The calculation of the time delay $t_{1-3}$ is identical.

For the determination of the time delay $t_{1-2}$, the central data-processing unit 10 initially determines for the first recording $a_n$ the moment ($t_1$) of the pulse wave passage by identifying some uniform point of the waveform. Next, for the second recording $b_n$, the moment ($t_2$) of appearance of the same pulse wave is determined by identifying the same uniform point of the pulse wave. The pulse wave velocity is determined by dividing the distance between the two points by the time it takes for the wave front to travel between those points. In practice, determining the wave front is difficult because of changes in pulse contour and amplitude as the wave propagates along the arterial tree. However, these changes in pulse contour and amplitude are not usually observed at the beginning of systole. For this reason, the time interval is preferably measured between the pressure wave foot (i.e., nadir).

The central data processing unit 10 calculates the time delay (difference in time of arrival) of the foot segment of the pulse waveform between $t_1$ and $t_2$ to obtain $t_{1-2}$. On the first (proximal) recording $a_n$, $t_1$ is defined as the time when the derivative of the recorded function reaches a maximum value. At the second (distal) pulse wave recordings, $b_n$, $t_2$ is defined by using the same method.

The transit time data is between the initial upstroke segment of the waveform of the arterial hemodynamic behavior data recorded at the proximal recording site and the initial upstroke segment of the waveform of the arterial hemodynamic behavior data recorded at the distal recording site. The initial upstroke segment of each recorded waveform is defined around the point at which the derivative of the recorded signal is maximal. The time delay between these two defined segments is measured according to a linear correlation method and at the moment when the linear correlation coefficient is maximal. The linear correlation is calculated between the two corresponding segments and repeated by shifting the distal waveform segment towards the proximal waveform segment, considered as fixed, by one time increment. This iterative process is continued over the whole calculation window, and is termed "time-shifting." The time shift associated with the maximal linear correlation coefficient represents the time displacement between the two segments and corresponds to the transit time.

More precisely, the $t_{1-2}$ is determined according to the following procedure:

Using a diagram of finished differences level 1, the maximal value, in absolute value, of the "derivative" of the first curve established from the first recording ($a_n$) is calculated, i.e. the C value defined as follows:

$$C = \{n \in IN \text{ such as } \forall_i \in [0, N-1] | a_{i+1} - a_i | \leq |a_{n+1} - a_n|\}$$

Thus, C corresponds to the index of the series, the digitized or discrete time version of the time trace $a_n$, where the difference between two successive elements is maximal.

$$C = \max |a_{n+1} - a_n|$$

$$0 \leq n \leq N-1$$

A C-centered work window $[m_0, M_0]$, is then defined, where $$m_0 = C - \text{Min Value}$$

$$M_0 = C + \text{Max Value}$$

The $k^{th}$ value, where $k \in [0, N-M_0]$, is the value that maximizes the linear correlation coefficient between the discrete curves $\bar{a} = (a_n)_{m_0 \leq n \leq M_0}$ and $\bar{b}_k = (b_{n+k})_{m_0 \leq n \leq M_0}$, i.e. the integer K of $[0, N-M_0]$ is given by:

$$\frac{\text{covar}(\bar{a}, \bar{b}_k)}{\sigma(\bar{a})\sigma(\bar{b}_k)} = \max_{k \in [0, N-M_0]} \left( \frac{\text{covar}(\bar{a}, \bar{b}_k)}{\sigma(\bar{a})\sigma(\bar{b}_k)} \right)$$

Finally, $t_2$ is determined as the moment corresponding to the K index in the second recording $b_n$. The delay $t_{1-2}$ is then calculated as $t_{1-2} = t_2 - t_1$.

The pulse velocity calculation in step 108 between arterial recording site $M_1$ and arterial recording site $M_2$, i.e., $v_{1-2}$, and the pulse velocity between arterial recording site $M_1$ and arterial recording site $M_3$, i.e., $v_{1-3}$, is performed by using $d_{1-2}$ and $d_{1-3}$ distances measured earlier, and from $t_{1-2}$ and $t_{1-3}$ time delays determined in step 106. For this calculation, the memory of the data processing unit 10 contains a d value representing the mean distance between the two recording sites ($M_1$ and $M_2$) or ($M_1$ and $M_3$). Indeed, the arterial pulse is generated at the heart and therefore the distances $d_{1-2}$ and $d_{1-3}$ may be corrected by subtracting from each the distance traveled in an opposite direction by the corresponding reflected pulse waves traveling the arterial system in the opposite direction. Thus, in step 108 illustrated in FIG. 2, the pulse wave velocities are calculated as:

$$v_{1-2} = \frac{d_{1-2} - d}{t_{1-2}} \quad \text{and} \quad v_{1-3} = \frac{d_{1-3} - d'}{t_{1-3}}$$

wherein d and d' represent the distances traveled by the pulse wave when, after bifurcation, it is propagated in opposite directions towards the arterial recording sites. For example, the distance d measured between the common carotid artery and the aorta is subtracted from the total distance measured between the carotid and femoral artery, since the pulse wave between the aorta and the common carotid artery is propagated in an ascending direction opposite to the descending direction between the aorta and the femoral artery. The distance d could also be determined by indirect means such as estimating the distance based, for example, on measurements of the patient's height, weight, and age and comparing these measurements to the mean distance in patients with similar height, weight, and age. Other factors might also be considered such as gender or body type. After calculation, the pulse wave velocities $v_{1-2}$ and $v_{1-3}$, are displayed on a display.

In the next steps, an estimation of the central aortic pulse pressure may be calculated by the central processing unit 10. Referring to FIG. 2, at step 110, the peripheral brachial pulse pressure of the patient is recorded from the brachial artery of the patient's arm in the usual manner with a stethoscope and blood pressure cuff or by other manual or automated devices for measuring the blood pressure. The brachial blood pressure is entered by the operator into the central processing unit 10.

At step 112, an estimate of the central aortic blood pressure is calculated by the central data processing unit 10 as follows. The aortic pulse wave velocity between an arterial recording site $M_1$ over the carotid artery, and an arterial recording site $M_2$, on the femoral artery, is calculated. The brachial pulse wave velocity between a recording site $M_1$ on the carotid artery and a recording site $M_3$ on the brachial artery is calculated. The aortic pulse pressure Pa is calculated using the relation:

$$Pb/Pa = \sqrt{Vb/Va}$$

wherein Va is the aortic pulse wave velocity, Vb is the brachial pulse wave velocity, and Pb is the brachial pulse pressure of the patient.

Thus, because of the non-uniformity of the patient's arterial distensibility, it is possible to determine from the brachial pulse pressure, a satisfactory estimate of the aortic pulse pressure.

With the method presented above for the determination of the delays $t_{1-2}$ and $t_{1-3}$, measurement precision is increased. Indeed, the use of the foot of the waveforms obtained from the recording sites allows, in conjunction with a correlation analysis between the different curves, a precise estimation of the time delay.

At step 114, the time delay extracted in step 106, the pulse wave velocity data extracted in step 108, or the aortic pulse pressure calculated in step 112, is compared to a reference value, standard, or to a preprogrammed library of normal and pathologic values for pulse wave time delays, pulse wave velocities, or aortic pressure to assess cardiovascular or systemic physiological status in the patient. The reference value can be a single value, multiple values, a single range, or multiple ranges. Thus, in one embodiment, the reference value is a plurality of predetermined pulse wave velocity ranges, and the comparison step comprises determining in which of the predetermined pulse wave velocity ranges, the individual's pulse wave velocity falls. Patient data that differs from the normal reference value, normal standard value, or normal values maintained in the preprogrammed library, is indicative of abnormal patient cardiovascular function. Patient data that correlates with pathologic reference values, pathologic standard values, or preprogrammed pathologic values is indicative of abnormal patient cardiovascular or systemic physiological status.

A patient's response to therapy can also be evaluated using the method according to the invention. The patient data is compared to a predetermined reference value, wherein the patient data in comparison to the predetermined value is indicative of the patient's response to therapy. The patient can then be characterized in terms of the benefit obtained by the therapy.

Figure 4:
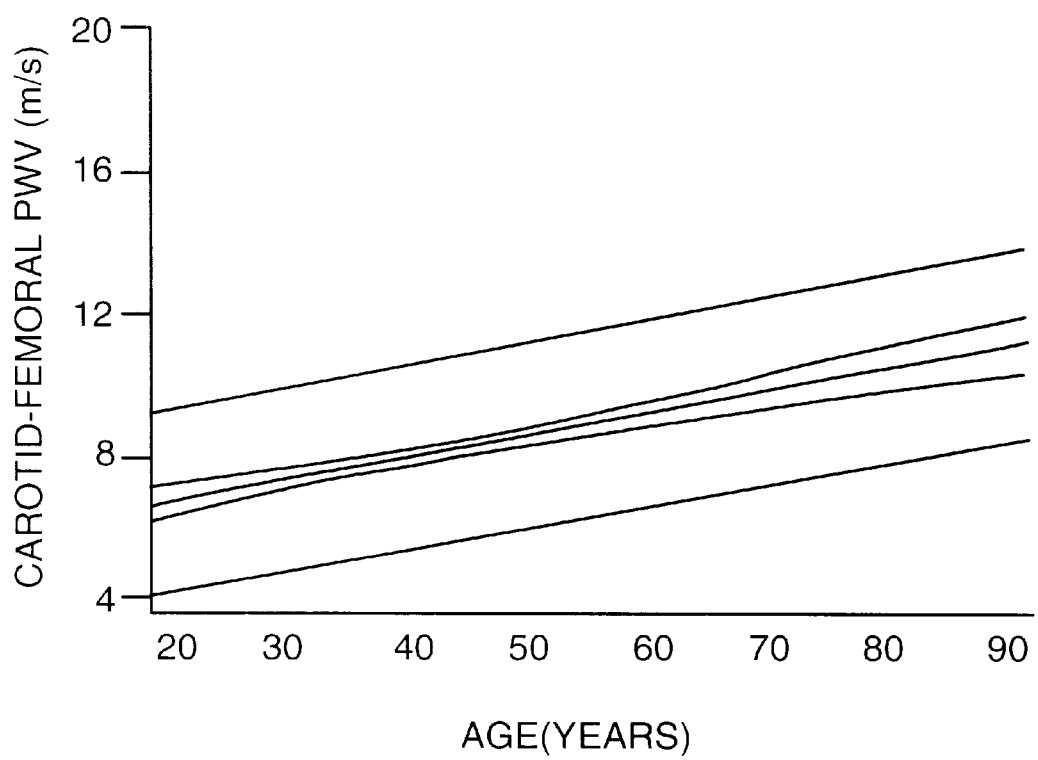
FIG. 4 is a plot of aortic pulse wave velocity (carotid-femoral PWV m/s) versus patient age (years) showing linear correlation (r=0.55) between PWV and age in normal subjects.

The central (trunk or aortic) pulse wave velocity of a patient may be compared to a reference value that reflects expected normal pulse wave velocity by measuring pulse wave velocity of normal individuals of similar age, gender, weight, etc., as the patient. As shown in FIG. 4, a linear correlation occurs between pulse wave velocity and age. As detailed in R. Asmar, Arterial Stiffness and Pulse Wave Velocity: Clinical Applications, Elsevier, N.Y., November, 1999, incorporated by reference herein, normal pulse wave velocity for a given patient of a certain age (x) can be calculated according to the following formula:

Pulse wave velocity (m/s)=0.0628(x)+5.728

The normal peripheral pulse wave velocity, for example, carotid-radial, brachial-radial, or femoro-tibial, for a given patient at a certain age, can be calculated according to this formula:

Pulse wave velocity (cm/s)=5.6x+791 for the leg and

Pulse wave velocity (cm/s)=4.8x+998 for the arm

Other factors may also be used to calculate a reference value for the normal expected pulse wave velocity of a patient. For example, systolic blood pressure may be used to calculate the estimated central (carotid-femoral) pulse wave velocity as follows:

Population as a whole:

Pulse wave velocity (m/s)=0.07 systolic blood pressure (mmHg)+ 0.09(age in years)−4.3

Normotensive subjects:

Pulse wave velocity (m/s)=0.06 systolic blood pressure (mmHg)+ 0.09(age in years)−2.3

Hypertensive subjects:

Pulse wave velocity (m/s)=0.06 systolic blood pressure (mmHg)+ 0.09(age in years)−2.7

Figure 5:
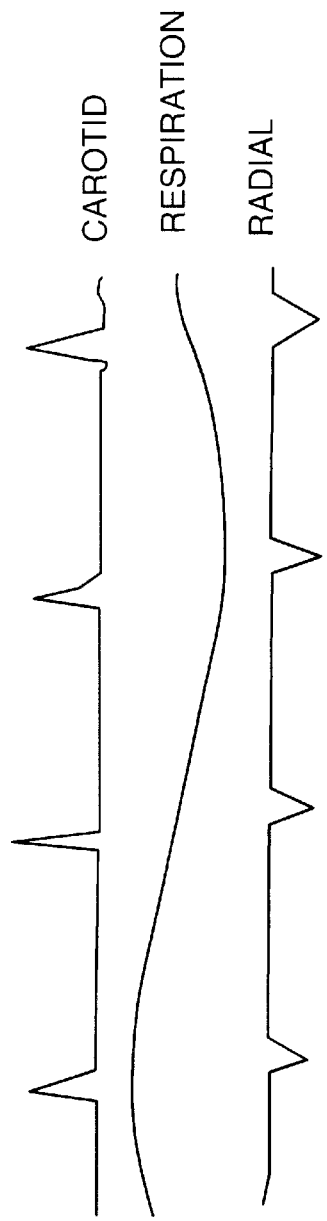
FIG. 5 shows recordings of carotid and radial pulse waves and respiration.
Figure 6:
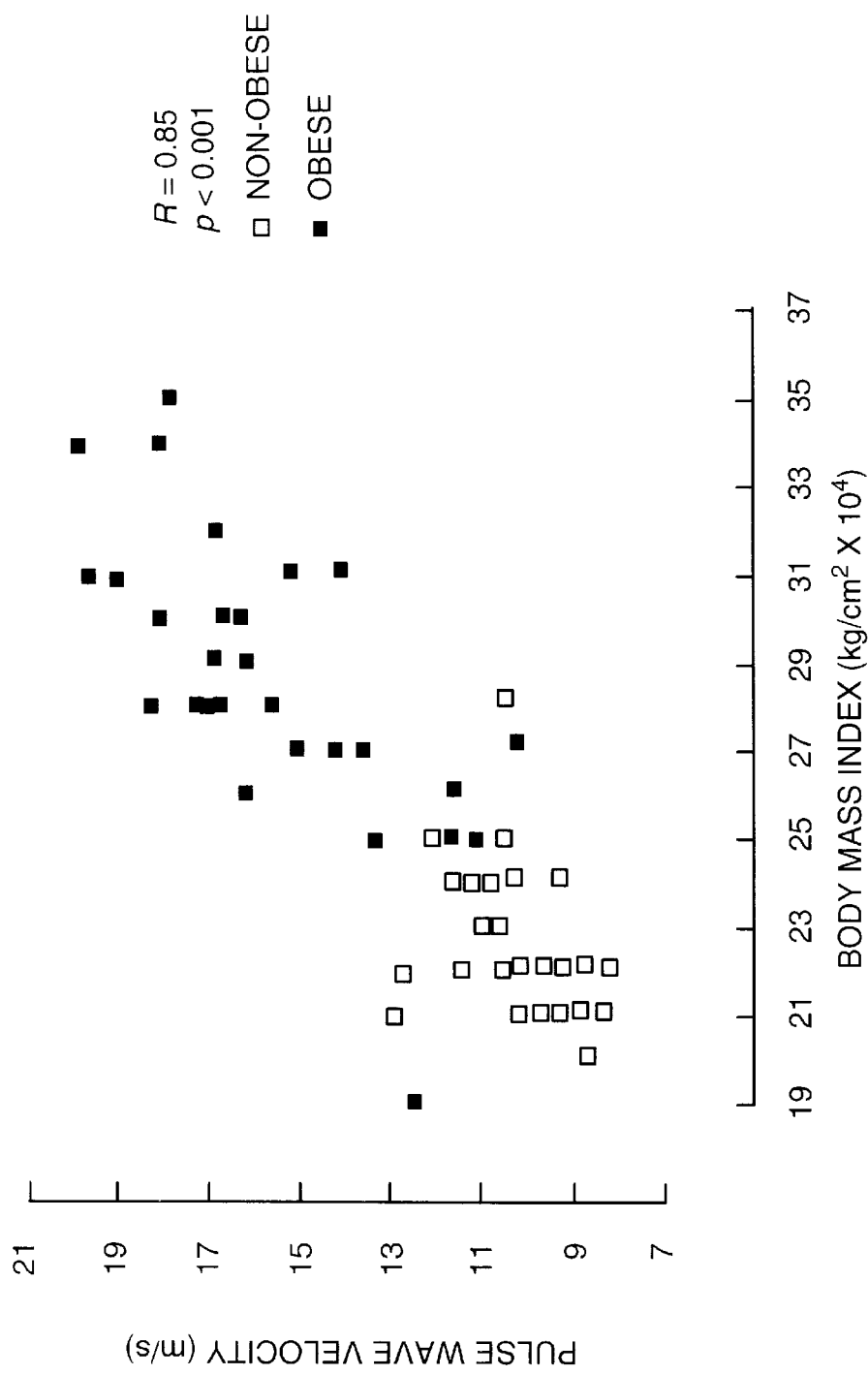
FIG. 6 is a scatter plot showing the relationship between body mass index (kg/cm$^2$×10$^4$) and brachial-radial PWV (m/s) in obese and non-obese hypertensive patients.
Figure 7:
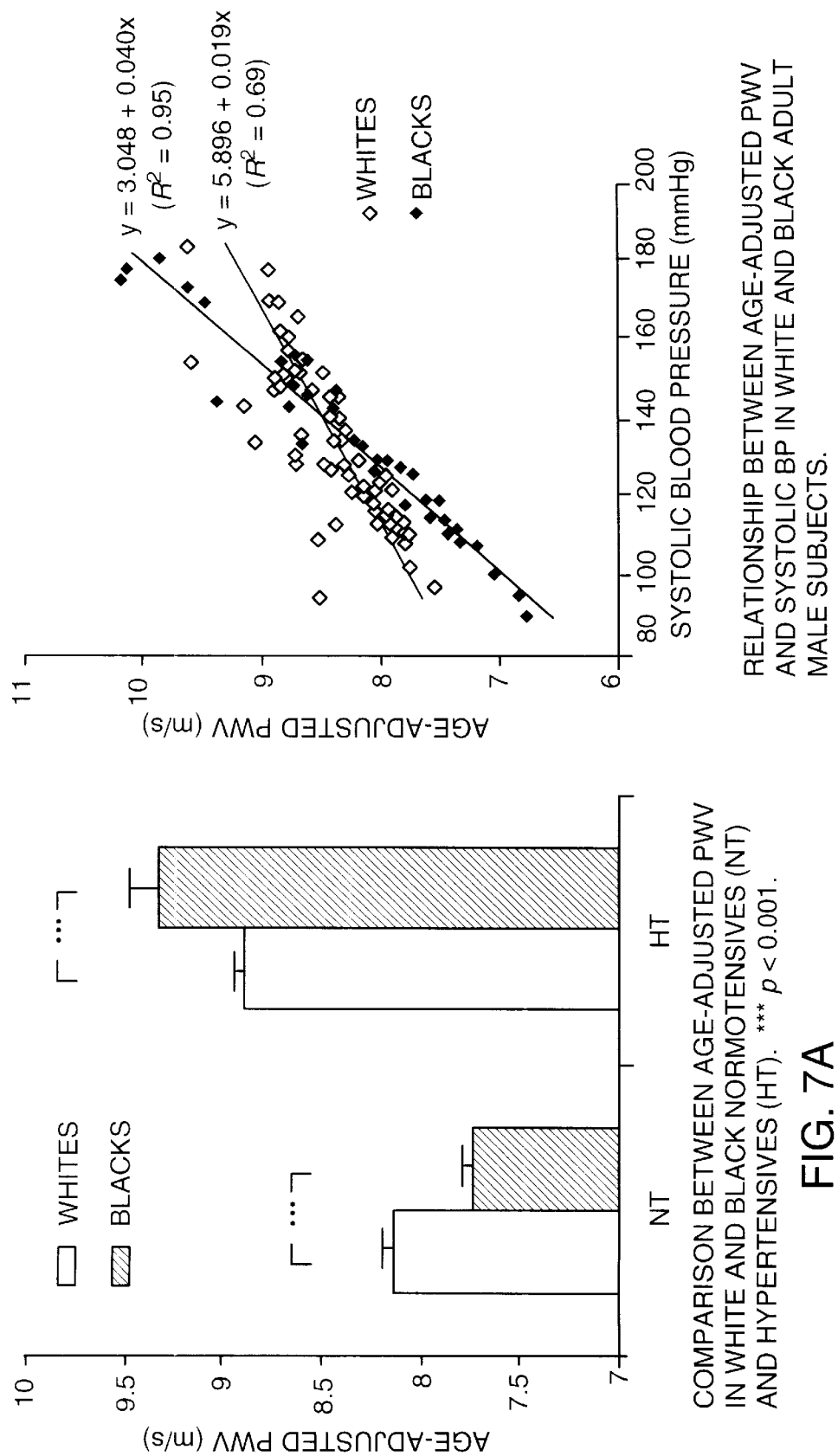
FIG. 7A is a column graph comparing age-adjusted PWV (m/s) in white and black normotensive (NT) and hypertensive (HT) patients.
FIG. 7B is a scatter plot comparing age-adjusted PWV (m/s) and systolic blood pressure in white and black adult male subjects.

Other factors that may be considered in determining a normal reference value for pulse wave velocity to be applied to a given patient are gender, heart rate, respiration (FIG. 5), food intake (Table 1), obesity, or body conformation (FIG. 6), and ethnicity (FIGS. 7A and 7B).

TABLE 1

Pulse Wave Velocity Measurements Before and After a Meal
PWV (m/s)

| Aorta | | Leg | | Arm | |
|---|---|---|---|---|---|
| Before Meal | After Meal | Before Meal | After Meal | Before Meal | After Meal |
| 4.36 ± 1.3 | 4.23 ± 0.8 | 8.06 ± 1.0 | 10.28 ± 1.8 | 9.55 ± 2.3 | 14.60 ± 4.6 |

The following examples will serve to better demonstrate the successful practice of the present invention.

Exemplification

As exemplification of the utility of systems, devices and methods of the invention, the following applications of the system, device, and method according to the invention are provided below. As will be appreciated by those of ordinary skill in the art, methods and compositions disclosed herein are applicable to other clinical applications for assessing cardiovascular function and physiological condition of a mammal.

EXAMPLE 1

Application of the Automatic Device for Measuring Pulse Wave Velocity According to the Invention to Assess Risk of Cardiovascular Disease In this study, pulse wave velocity as a cardiovascular disease risk marker was studied in a cohort of 710 patients with essential hypertension. Measurements were performed in patients with and without atherosclerosis. The pulse wave velocity measurement was performed using the automatic device and method according to the invention which allowed an online pulse wave recording and automatic calculation of pulse wave velocity with two pressure transducers, one positioned at the base of the neck for the common carotid artery, and the other transducer placed over the femoral artery. Validation of the automatic method was demonstrated by reproducibility of results with an interobserver repeatability coefficient of 0.935 and an intraobserver coefficient of 0.890.

Pulse wave velocity was higher in patients with atherosclerosis (14.9±4.0 versus 12.4±2.6 m/s; patients with atherosclerosis versus patients without atherosclerosis, respectively; $P<0.0001$) even after adjustments on confounding factors, and was the first determinant ($P<0.0001$) of the extent of atherosclerosis assessed as the sum of the atherosclerotic sites. In patients without atherosclerosis, all cardiovascular risks increased constantly with pulse wave velocity. At a given age, aortic pulse wave velocity, measured by the automatic device according to the invention, was the best predictor of cardiovascular mortality. The presence of pulse wave velocity greater than 13 m/s, taken alone, appeared as a strong predictor of cardiovascular mortality. This study demonstrates that aortic pulse wave velocity assessed by the device and method according to the invention is strongly associated with the presence and extent of atherosclerosis and constitutes a forceful marker and predictor of cardiovascular risk in hypertensive patients.

EXAMPLE 2

Application of the Automatic Device for Measuring Pulse Wave Velocity According to the Invention Correlated with Plasma Levels of Homocysteine for Assessment of Cardiovascular Disease Risk in Hypertensive Patients In this study, pulse wave velocity coordinated with plasma homocysteine levels were studied as indicators of cardiovascular disease risk in 236 male and female hypertensive patients. The pulse wave velocity was measured according to the automatic device and method of the invention which allows an online pulse wave recording and automatic calculation of pulse wave velocity. Common carotid artery and femoral artery pressure waveforms were measured non-invasively using a TY-306 Fukuda pressure-sensitive transducer (Fukuda, Tokyo, Japan). The pressure waveforms were digitized at the sample acquisition frequency of 500 Hz. The two acquired pressure waveforms, one from the carotid artery and one from the femoral artery, were stored in a memory buffer. A preprocessing system analyzed the gain in each waveform and adjusted the gain equally for equality of the two signals. When the operator observed a pulse waveform of sufficient quality on the computer screen, digitization was suspended and calculation of the time delay between two pressure upstrokes was taken. Measurement was repeated over at least ten different cardiac cycles, and the mean was used for the final analysis. The distance traveled by the pulse wave was measured over the body surface as the distance between the two recording sites ($d_1$ and $d_2$) while pulse transit time (t), measured between the feet of the pressure waveforms recorded at these different points (foot-to-foot method), was automatically determined according to the device and method of the invention.

In the population studied, pulse wave velocity was positively correlated with plasma homocysteine according to the extent of atherosclerosis. The results of this study show that evaluation of aortic distensibility by determining pulse wave velocity by the device and method according to the invention, and correlated with other measured patient criteria, such as plasma, homocysteine levels, can help in cardiovascular disease risk assessment in hypertensive patients (*Hypertension* (1999) 34: 837–842).

EXAMPLE 3

Application of the Automatic Device and Method for Measuring Pulse Wave Velocity According to the Invention to Monitor Therapy of Hypertensive Patients In this double-blind study, pulse wave velocity as determined by the device and method according to the invention, was used to follow the effect of therapy in patients with hypertensive disease.

Aortic pulse wave velocity was determined by the automatic device and method according to the invention described above. Briefly, common carotid artery and femoral artery pressure wave forms were recorded non-invasively with a TY-306-Fukuda pressure sensitive transducer (Fukuda, Tokyo, Japan). The pressure waveforms were digitized at the sample acquisition frequency of 500 Hz. The two pressure waveforms were then stored in a memory bank. A preprocessing system automatically analyzed the gain in each waveform and adjusted it to equalize the two signals. When the operator observed a pulse waveform of sufficient quality on the computer screen, digitization was suspended, and calculation of the time delay ($t_{1-2}$) between the first pressure upstrokes ($t_1$) and the second pressure upstroke ($t_2$) was initiated. Measurement was repeated over ten cardiac cycles, and the mean was used for the final analysis. The distance ($d_{1-2}$) traveled by the pulse wave was measured over the surface of the body as the distance between the first recording site ($d_1$) and the second recording site ($d_2$). Pulse wave velocity was automatically calculated as pulse wave velocity=$d_{1-2}/t$.

The study was done over 180 days on three hypertensive patient groups treated with verapamil, trandolapril, or their combination. Pulse wave velocity as determined by the device and method according to the invention, was significantly reduced (p<0.01) in patients treated with verapamil (13±4 versus 11±3 m/s), trandolapril (13±2 versus 11±3 m/s) and combination of verapamil and trandolapril (13±2 versus 11±2 m/s).

The results obtained in this study for pulse wave velocity were correlated with improved systolic, diastolic, and mean blood pressure, improved cardiac and carotid artery structure as determined by ultrasound and echocardiography, respectively, and improved distensibility and diameter of the carotid artery, brachial artery and aorta as determined by an original pulsed ultrasound echo-tracking system. Thus, pulse wave velocity, as measured by the device and method according to the invention described above, is useful for monitoring the progression of cardiovascular disease and for monitoring the effect of therapy in patients (*Stroke* (1999) 30: 1056–1064).

EXAMPLE 4

Application of the Device and Method for Measuring Pulse Wave Velocity According to the Invention to Monitor Therapy of Normotensive Patients This study was carried out in post-menopausal patients to evaluate the effect of estrogen on blood pressure and arterial distensibility, the latter determined by measurement of pulse wave velocity.

The study was conducted on 17 normotensive, post-menopausal untreated women following hysterectomy and bilateral ooforectomy. Blood pressure recording was performed non-invasively and aortic distensibility was evaluated by carotid-femoral artery pulse wave velocity using the automatic device and method according to the invention described above. All women were submitted to two evaluations: basal (<3 months after surgery), and after 6 months of transdermic estrogen (a 50 µg patch of 17β-estradiol).

Results of the study indicated no difference in systolic or diastolic blood pressure after six months of estrogen replacement therapy. However, significant improvement in arterial distensibility, evaluated by measurements of pulse wave velocity by the automatic device and method according to the invention (12±3 m/s versus 10±2 m/s; P<0.001) was observed after 6 months of estrogen replacement therapy.

The results of these studies indicate that the automatic device and method according to the invention may be used to assess the effect of therapy on cardiovascular function in a patient when the presence of cardiovascular disease is not otherwise evidenced by conventional means of assessing cardiovascular function in the patient.

EXAMPLE 5

Figure 8:
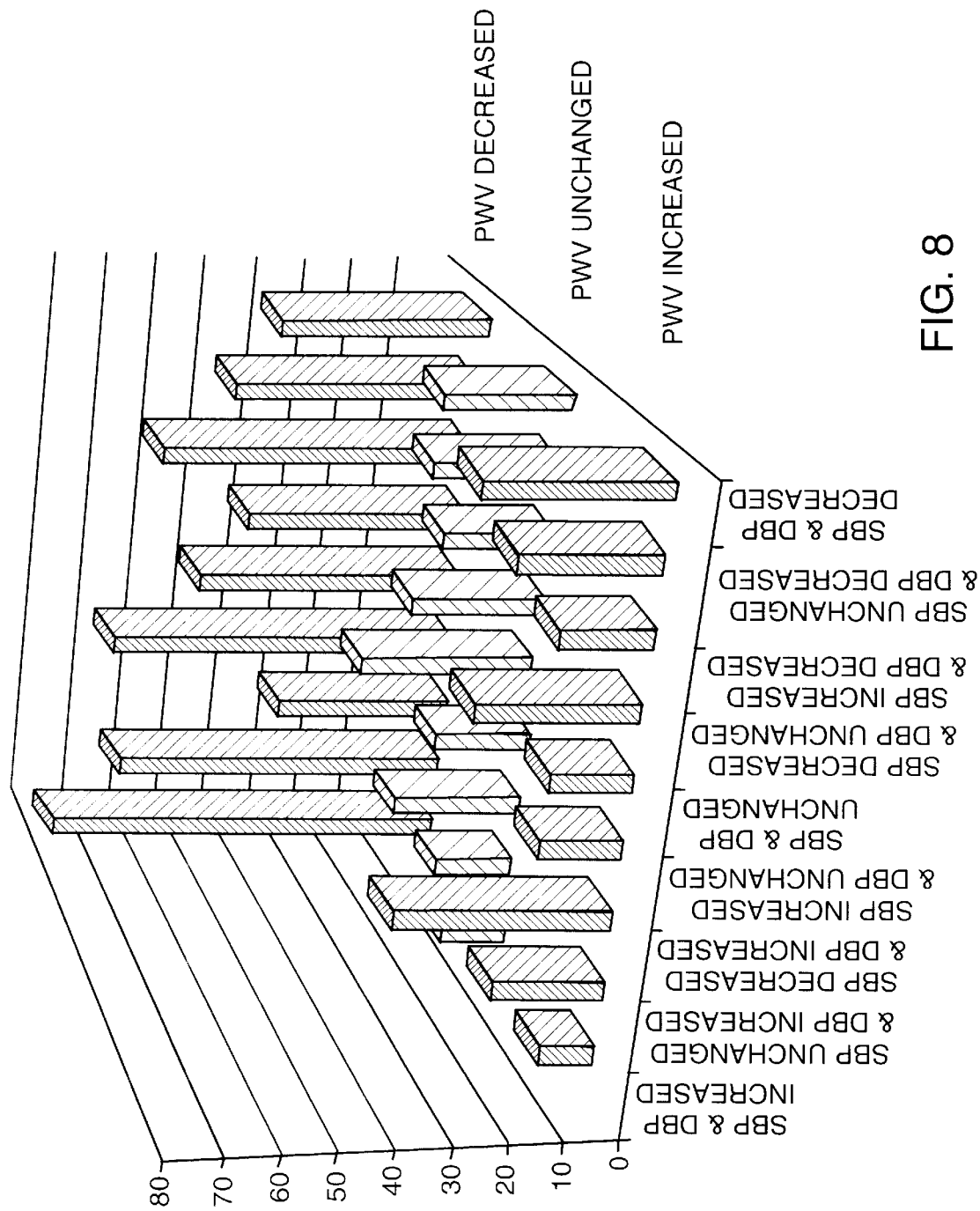
FIG. 8 shows distribution of pulse wave velocity variations (%) in relation to changes in diastolic (DBP) and systolic (SBP) blood pressure.

Application of the Device and Method for Measuring Pulse Wave Velocity According to the Invention for Monitoring Therapy of Hypertensive Patients This study was carried out in a large-population clinical trial designed to evaluate the ability of an antihypertensive therapy to improve the arterial abnormalities observed in hypertension. Patients were treated for six months, starting with perindopril 4 mg daily which was increased to 8 mg daily, and combined with a diuretic (indapamide 2.5 mg daily) if blood pressure was uncontrolled (>140/90 mmHg). Arterial stiffness was assessed before treatment, and at two and six months after treatment, by carotid-femoral pulse wave velocity measurements, using the device and method described above according to the invention. Data collected from 69 centers (19 countries) concerned more than 2,000 patients. The results showed significant (p<0.001) decreases from baseline in blood pressure (systolic (SBP):−23.7±16.8, diastolic (DBP): −14.6±10 mmHg), and pulse wave velocity (−1.1±1.4 m/s). Despite a significant correlation (p<0.001) between changes in systolic blood pressure and pulse wave velocity, less than 10% ($r^2$=0.06) of the observed arterial effects were related to blood pressure reduction. Individual analysis showed that pulse wave velocity improvement was not always concomitant with blood pressure reduction, and vice versa, as given in Table 2 and FIG. 8, suggesting a specific arterial effect of the study drug regimen. This study shows that arterial abnormalities observed in a hypertension can be followed by assessing pulse wave velocity according to the invention during antihypertensive therapy.

TABLE 2

Blood Pressure and Carotid-Femoral PWV, Mean Values and Changes From Baseline (M0) After Six Month Treatment (M6)

| Variables | M0 | M6 | ΔM6-M0 | p |
|---|---|---|---|---|
| SBP (mmHg) | 158 ± 15 | 134 ± 13 | −24 − 17 | <0.001 |
| DBP (mmHg) | 98 ± 7 | 84 ± 8 | −14 ± 10 | <0.001 |
| MBP (mmHg) | 118 ± 8 | 100 ± 9 | −18 ± 11 | <0.001 |
| PP (mmHg) | 59 ± 15 | 50 ± 10 | −9 ± 15 | <0.001 |
| HR (bpm) | 75 ± 10 | 75 ± 10 | −0.3 ± 10 | NS |
| PWV (m/s) | 11.6 ± 2.6 | 10.5 ± 2.1 | −1.1 ± 1.4 | <0.001 |

Variations, modifications, and other implementations of what is described herein will occur to those of ordinary skill in the art without departing from the spirit and scope of the invention as claimed. Accordingly, the invention is to be defined, not by the preceding illustrative description but instead by the spirit and scope of the following claims.

What is claimed is:

1. A method for assessing cardiovascular function in a patient comprising the steps of:
   obtaining arterial hemodynamic behavior data from the patient at a first recording location;
   obtaining arterial hemodynamic behavior data from the patient at at least a second recording location;
   extracting data indicative of transit time of the arterial hemodynamic behavior data obtained between the first recording location and second recording location;
   measuring distance between the first recording location and the second recording location to obtain distance data;
   determining arterial hemodynamic behavior velocity data from the transit time data and the measured distance data; and
   correlating the arterial hemodynamic behavior velocity data with a reference value to determine cardiovascular function in the patient.

2. The method of claim 1 wherein the arterial hemodynamic behavior at the second recording location is obtained simultaneously with the arterial hemodynamic behavior obtained at the first recording location.

3. The method of claim 1 further comprising the steps of:
   obtaining arterial hemodynamic behavior data from the patient at a third recording location;
   extracting data indicative of transit time of the arterial hemodynamic behavior data obtained between the first location and the third location;
   measuring distance between the first recording location and the third recording location to obtain distance data;
   determining arterial hemodynamic velocity data from the transit time data and the measured distance data between the first recording location and the third recording location;
   and correlating the arterial hemodynamic behavior velocity data between the first recording location and the third recording location with a reference value to determine cardiovascular function in the patient.

4. The method of claim 1 further comprising the step of smoothing the data obtained at the first recording location and at the second recording location.

5. The method of claim 4 wherein the smoothing step comprises a low-pass filtering algorithm to process each recording.

6. The method of claim 1 wherein the first recording location is located at a proximal position on an artery and the second recording location is located at a position along an arterial tree distal to the first recording location.

7. The method of claim 1 wherein the first recording location is located over the common carotid artery near the base of the neck of the patient and the second recording location is located over a femoral artery of the patient.

8. The method of claim 1 further comprising the step of digitizing the arterial hemodynamic behavior data obtained from the first recording location and the second recording location.

9. The method of claim 1 wherein the arterial hemodynamic behavior data comprises pulse pressure wave data.

10. The method of claim 1 wherein the arterial hemodynamic behavior data comprises pulse volume wave data.

11. The method of claim 1 wherein the arterial hemodynamic behavior data comprises pulse flow wave data.

12. The method of claim 1 wherein the arterial hemodynamic behavior data comprises arterial diameter wave data.

13. The method of claim 1 further comprising the step of displaying transit time data indicative of cardiovascular function in the patient.

14. The method of claim 1 further comprising the step of displaying the velocity data indicative of cardiovascular function in the patient.

15. The method of claim 1 further comprising obtaining arterial hemodynamic behavior data at a first recording location and at a second recording location during a plurality of respiratory cycles.

16. The method of claim 1 further comprising obtaining arterial hemodynamic behavior at a first recording location and at a second recording location during at least one complete respiratory cycle.

17. The method of claim 1 further comprising the step of comparing the arterial hemodynamic velocity data of the patient with a reference value, wherein a difference in the arterial hemodynamic velocity data of the patient compared to the reference value is indicative of abnormal cardiovascular function of the patient.

18. The method of claim 1 further comprising the step of comparing the arterial hemodynamic behavior velocity data of the patient with arterial hemodynamic behavior velocity data in a preprogrammed library of arterial hemodynamic behavior data in normal and pathologic cardiovascular function, wherein differences between the arterial hemodynamic behavior velocity data of the patient and the arterial hemodynamic behavior velocity data of normal or pathological cardiovascular function, is indicative of cardiovascular function of the patient.

19. The method of claim 1 wherein the cardiovascular function comprises arterial distensibility.

20. A system for assessing cardiovascular function in a mammal, comprising:
   a first transducer for recording arterial hemodynamic behavior data at a proximal recording site;
   at least a second transducer for recording arterial hemodynamic behavior data at a second recording site distal to said proximal recording site;
   a data processor for extracting transit time data between an initial upstroke segment of a waveform of the arterial hemodynamic behavior data recorded at the proximal recording site and an initial upstroke segment of a waveform of the arterial hemodynamic behavior data recorded at the distal recording site by repetitively shifting the distal waveform segment toward the proximal waveform segment, wherein the initial upstroke of the waveform recorded at the proximal recording site is determined, and the initial upstroke of the waveform recorded at the distal recording site is determined when a coefficient of correlation is maximal when comparing corresponding areas around the beginning of the upstroke of the waveform recorded at the proximal recording site and at the distal recording site; and an apparatus for measuring a distance between the first recording site and the second recording site to obtain measured distance data, wherein the processor extracts arterial hemodynamic velocity data from the transit time data and the measured distance data to assess cardiovascular function in the mammal.

21. The system of claim 20 wherein the transducers obtain arterial hemodynamic data comprising arterial diameter data.

22. The system of claim 20 further comprising a display for displaying the arterial hemodynamic velocity data.

23. The system of claim 20 further comprising an analog to digital converter for converting the arterial hemodynamic behavior data from analog form to digital form.

24. The system of claim 20 wherein the transducers obtain arterial hemodynamic data comprising pulse flow data.

25. The system of claim 20 wherein the transducers obtain arterial hemodynamic data comprising pulse pressure data.

26. The system of claim 20 wherein the transducers obtain arterial hemodynamic data comprising pulse volume data.

27. The system of claim 19 further comprising a filter to filter out high frequency noise.

28. The system of claim 27 wherein the filter comprises a low-pass filtering algorithm.

29. A method for determining the time delay between a proximal and a distal recording site over a patient arterial system, comprising the steps of:
 a) measuring a distance between two recording sites over the arterial system of the patient;
 b) obtaining simultaneous pulse arterial data in waveform at the two recording sites;
 c) calculation of the pulse wave time between the two recording sites as follows:
  i) at the first recording site, determine a proximal waveform by identifying a footwave at a beginning of an initial upstroke;
  ii) at the second recording site, determine a distal waveform by identifying a footwave of an initial upstroke by searching in the second recording when a coefficient of correlation is maximal when comparing corresponding areas around the proximal and distal waveforms;
  iii) determine transit time delay between the two corresponding footwaves in the proximal and distal pulse waveforms; and
 d) extracting pulse wave velocity from the distance between the two recording sites determined in step (a) and the transit time calculated in step (c) using a processor.

30. The method of claim 29 wherein the arterial pulse data is obtained at two recording sites during at least one respiratory cycle.

31. The method of claim 30 further comprising calculating the pulse wave velocity from the measured distance between the first and second recording sites and the transit time delay of the proximal and distal waveforms.

32. A method for determining aortic pulse pressure in a patient, comprising the steps of:
 a) determining aortic pulse wave velocity between a first recording site on a carotid artery of the patient and a second recording site on a femoral artery of the patient;
 b) determining brachial pulse wave velocity between a first recording site on the carotid artery of the patient and a third recording site on a brachial artery of the patient;
 c) measuring brachial pulse pressure; and
 d) extracting the aortic pulse pressure from the aortic and brachial pulse wave velocities, and from the measured brachial pulse pressure, wherein the aortic pulse pressure $P_a$ is determined using the relation:

$$Pb/Pa = \sqrt{Vb/Va}$$

wherein, $V_a$ is the aortic pulse wave velocity, $V_b$ is the brachial pulse wave velocity, and $P_b$ is the brachial pulse pressure.

33. A method for assessing cardiovascular function in a patient comprising the steps of:
 applying a transducer to each of a proximal recording site and at least one distal recording site over the patient's arterial system;
 simultaneously recording an arterial pulse in wave form at the proximal recording site and at least one of the distal recording sites;
 calculating transit time of the arterial pulse waveform between the proximal recording site and at least one of the distal recording sites comprising the steps of:
  identifying a segment on an initial upstroke of the proximal waveform recorded at the proximal recording site;
  identifying a segment on an initial upstroke of the at least one distal recording sites corresponding to the segment identified on the proximal waveform;
  determining the transit time from a time delay between the segment identified on the proximal waveform and the corresponding segment identified on the distal waveform;
 determining a distance between the proximal recording site and the at least one distal recording site;
 calculating velocity of the pulse wave from the proximal recording site to at least one distal recording site from the determined transit time and the determined distance between the proximal recording site and the distal recording site; and
 comparing the pulse wave velocity of the patient to a reference value, wherein a difference between the pulse wave velocity in the patient and the reference value is indicative of abnormal patient cardiovascular function.

34. The method according to claim 33 wherein the initial upstroke of the waveform comprises a time at which a derivative of the recording at the proximal recording site or the distal recording site is maximal.

35. The method according to claim 33 wherein identification of the initial upstroke in the distal waveform comprises searching in the distal recording for a moment when a coefficient of correlation is maximal when comparing corresponding areas around the initial upstroke of the proximal waveform and the initial upstroke of the-distal waveform.

36. The method according to claim 35 wherein the correlation coefficient is linear.

37. A method for determining central aortic pulse pressure of a patient comprising the steps of:

calculating central aortic hemodynamic behavior velocity between a recording site on a carotid artery and a recording site on a femoral artery;

calculating peripheral brachial hemodynamic behavior velocity between a recording site on the carotid artery and a recording site on a brachial artery;

measuring brachial pulse pressure; and calculating the central aortic pulse pressure from the calculated aortic hemodynamic behavior velocity, the calculated brachial hemodynamic behavior velocity, and the brachial pulse pressure.

* * * * *